United States Patent [19]

Tieman et al.

[11] 4,299,843
[45] Nov. 10, 1981

[54] STABILIZED CYANDHYDRIN ESTER

[75] Inventors: Charles H. Tieman; Samuel B. Soloway, both of Modesto, Calif.

[73] Assignee: Shell Oil Company, Houston, Tex.

[21] Appl. No.: 82,243

[22] Filed: Oct. 5, 1979

Related U.S. Application Data

[63] Continuation-in-part of Ser. No. 10,292, Feb. 8, 1979, abandoned, which is a continuation-in-part of Ser. No. 891,773, Mar. 30, 1978, which is a continuation-in-part of Ser. No. 836,628, Sep. 26, 1977, abandoned.

[51] Int. Cl.³ .................... A01N 37/34; A01N 37/00
[52] U.S. Cl. .................................... 424/304; 424/317
[58] Field of Search ............................... 424/304, 317

[56] References Cited

U.S. PATENT DOCUMENTS

| | | | |
|---|---|---|---|
| 3,835,176 | 9/1974 | Matsuo et al. | 424/304 |
| 3,914,274 | 10/1975 | Searle et al. | 424/304 |
| 4,053,612 | 10/1977 | Bause et al. | 424/304 |
| 4,062,968 | 12/1977 | Fujimoto et al. | 424/304 |
| 4,110,360 | 8/1978 | Sheldon et al. | 260/465 D |

FOREIGN PATENT DOCUMENTS

| | | | |
|---|---|---|---|
| 2386259 | 8/1978 | France | 424/304 |
| 2396507 | 9/1979 | France | 424/304 |

OTHER PUBLICATIONS

Elliott et al., "Nature", vol. 246, (1973), p. 169–170.

*Primary Examiner*—Douglas W. Robinson

[57] ABSTRACT

A pesticidal composition comprising a major amount of a nonracemic form of a pesticidally effective cyanohydrin ester or a solution of the non-racemic ester in a solvent and a stabilizing amount of an acid or acidic acting material.

29 Claims, No Drawings

STABILIZED CYANDHYDRIN ESTER

CROSS-REFERENCE TO RELATED APPLICATIONS

This application is a continuation-in-part of Ser. No. 10,292, filed Feb. 8, 1979, now abandoned, which is a continuation-in-part of Ser. No. 891,773, filed Mar. 30, 1978, which is a continuation-in-part of Ser. No. 836,628, filed Sept. 26, 1977, now abandoned.

BACKGROUND OF THE INVENTION

1. Field of the Invention

The present invention is directed to a stabilized, non-racemic form of a cyanohydrin ester.

2. Description of the Prior Art

Certain esters of substituted cyclopropanecarboxylic acids and substituted phenylacetic acids are a useful class of pesticides known as "pyrethroids". These pyrethroids, especially the more recent synthetic ones, are of considerable interest because of their high insecticidal activity, quick knockdown activity, low persistence as toxic residues and their low mammalian toxicity.

The pyrethroids can exist in the form of optical isomers, cis-trans isomers and other kinds of geometric isomers depending on the particular substituent groups. These various isomers may have different pesticidal toxicities and/or knockdown potency. Thus, one may prefer to resolve (racemic) mixtures of isomers to recover a more pesticidally active isomer or isomer mixture or one may prepare a more active isomer or isomer mixture directly.

For example, in the case of certain cyanohydrin esters containing at least one asymmetric carbon atom in each of the acid and alcohol moieties, the individual diastereoisomers containing the (+)-R-stereoisomer configuration in the alcohol moiety are significantly less active than the individual diastereoisomers containing the (−)-S-stereoisomer configuration. Thus, it is desirable to prepare the more pesticidally active stereoisomers or non-racemic mixtures enriched in the more pesticidally active stereoisomer. An example of such a mixture is an enantiomer pair containing the more pesticidally active stereoisomer configuration. Direct synthesis or mixture enrichment with respect to a more pesticidally active non-racemic form of cyanohydrin esters is desirable and now possible by base-catalyzed epimerization (as hereinafter described in this application and in U.S. Pat. Nos. 4,133,826 and 4,151,195). Moreover, it is desirable to prevent reverse epimerization of the non-racemic ester back toward the starting racemic or diastereoisomer mixture.

SUMMARY OF THE INVENTION

The invention is based on the finding that the addition of a stabilizing amount of an acid to a non-racemic form of a cyanohydrin ester, or to a solution thereof in a solvent, functions to prevent base-catalyzed epimerization toward a more equilibrium mixture of stereoisomers, such as a racemic or diastereoisomer mixture. This stabilization is useful, e.g., during recrystallization, storage or formulation, of a product non-racemic cyanohydrin ester as even glass containers or denaturants added to alkanol solvents reduce the stability of the non-racemic forms.

While the precise amount of acid to stabilize the stereoisomer may vary depending upon the particular cyanohydrin ester, from about 0.001 to about 5% by weight of acid based on the non-racemic cyanohydrin ester is generally sufficient. Preferably, from 0.01 to 0.5% by weight of acid is used.

Any inorganic or organic acid or acidic acting material can be used, which will impart an acidic character to the cyanohydrin ester or solution thereof, including acidic clays such as acidic silicates and aluminates or synthetic acidified clays, mineral acids such as hydrochloric or sulfuric acid, sulfonic acids such as toluenesulfonic acid, or organic acids, including lower alkanoic acids containing from 1 to 7 or preferably 2 to 4 carbon atoms, such as acetic, propionic or butyric acids. The acid can be used in a solid or liquid form.

Stabilized pesticidal formulations not only include a pesticidally effective non-racemic cyanohydrin pyrethroid ester and stabilizing acidic material but can also contain solvents, surface-active agents and the like. When the stabilizing material is an acidic clay, it can also serve as the carrier. When the stabilizing agent is an acidic surface-active agent, e.g., acidic emulsifier, it can serve as both the stabilizer and emulsifier.

The solvent is usefully any of the solvents normally employed in the epimerization process used to prepare the non-racemic ester or any agriculturally acceptable solvent.

Examples of suitable classes of solvents include chlorinated hydrocarbons, ethers, nitriles, esters, hydroxylic solvents and the like. Suitable hydroxylic solvents include lower alkanols containing from 1 to 4 carbon atoms such as isopropanol, butanol, ethanol, and methanol, and preferably containing from 1 to 2 carbon atoms, especially methanol. Other suitable solvents are alkanes containing from 5 to 10 carbon atoms such as n-petane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80 and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene. Ethers are generally those containing from 4 to 6 carbon atoms such as diethyl ether, methyl tert-butyl ether and diisopropyl ether. Tetrahydrofuran and dioxane are also useful. Nitriles usually also contain from 2 to 6 carbon atoms, for example, acetonitrile and the like. Esters are those of lower alcohols and acids each containing from 2 to 6 carbon atoms, for example, ethyl acetate.

The present compositions comprise a major amount of a cyanohydrin ester, which contains at least one asymmetric carbon atom in each of the acid and alcohol moieties. Stereoisomers of such esters which are not mirror images are called diastereoisomers and those stereoisomers which are mirror images are called enantiomers. The present compositions comprise a non-racemic form of such pesticidally effective cyanohydrin esters and thus the non-racemic form may be an enantiomer pair, a single diastereoisomer or a mixture enriched in a desired enantiomer pair or single diastereoisomer.

The cyanohydrin esters which can be used in the invention include those cyanohydrin esters of the pyrethroid type. Typical cyanohydrin esters have the formula I

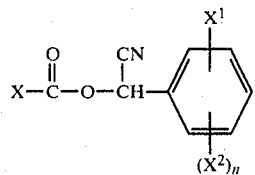

wherein X is a substituted benzyl or a substituted cyclopropyl group containing at last one asymmetric carbon atom, $X^1$ is phenoxy, benzyl or phenylthio, $X^2$ is a halogen atom having an atomic number of from 9 to 35, inclusive, or is methyl and n is 0, 1 or 2.

Preferred because of their pesticidal properties are those pyrethroid esters of formula I wherein n is O and $X^1$ is located in the 3-position relative to the benzyl carbon atom in the alcohol moiety. Especially useful are those pyrethroid esters of formula I wherein $X^1$ is phenoxy.

When X represents a substituted benzyl group in formula I, preferred compounds are those containing a substituted benzyl group of the formula II

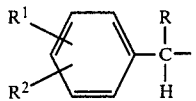

wherein R is an alkyl, cycloalkyl or alkenyl group containing up to 4 carbon atoms and $R^1$ is a hydrogen atom, a halogen atom having an atomic number of from 9 to 53, inclusive, or an alkyl group containing from 1 to 4 carbon atoms or an alkoxy group containing from 1 to 2 carbon atoms, each optionally substituted by one or more halogen atoms having an atomic number of from 9 to 53, inclusive, and $R^2$ is a hydrogen atom or a methyl group.

Preferred because of their pesticidal properties are those pyrethroids wherein X is a substituted benzyl group of formula II in which R is a branched-chain alkyl or alkenyl group containing 3 or 4 carbon atoms, such as isopropyl or isopropenyl, $R^1$ is a halogen atom or an alkyl or alkoxy group as defined above, for example, $R^1$ is a chlorine or fluorine atom, methyl, ethyl, isopropyl, tert-butyl, methoxy, ethoxy, difluoromethoxy or trifluoromethoxy and $R^2$ is a hydrogen atom. $R^1$ can be located at the meta- or para-position relative to the benzyl carbon atom in the acid moiety. Preferably, $R^1$ is located at the para-position.

When X represents a substituted cyclopropyl group in formula I, preferred compounds are those containing a cyclopropyl group of the formula III

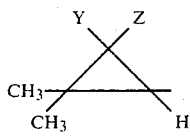

wherein Y and Z each is a halogen atom having an atomic number of from 9 to 35, inclusive, or Y is a halogen atom, an isobutenyl group, a 2,2-dihalovinyl group in which each halo is a halogen atom having an atomic number of from 9 to 35, inclusive, and Z is a hydrogen atom.

Preferred because of their pesticidal properties are those pyrethroids wherein X is a cyclopropyl grooup of formula III in which Y and Z each is chlorine or Y is chlorine, isobutenyl, 2,2-dichlorovinyl or 2,2-dibromovinyl and Z is a hydrogen atom.

In the case of the cyanohydrin esters described above, a single stereoisomer or enantiomer pair or a mixture enriched in such a material is prepared by contacting a diastereoisomer mixture or racemic mixture (as appropriate) with a base as an epimerization catalyst, in the presence of a solvent from which said stereoisomer or enantiomer pair preferentially crystallizes, at a temperature below the melting point of the desired single stereoisomer, to obtain the single desired stereoisomer or enantiomer pair (in high purity) as a syrup or solid phase, at least in a quantity (substantially) in excess of the amount originally present in the starting diastereoisomer mixture.

A diastereoisomer mixture of cyanohydrin esters for the purpose of the method of the present application is defined as one in which the diastereoisomers differ in configuration only at the asymmetric carbon atom in the alcohol moiety containing the cyano substituent.

For example, in the case of either alpha-cyano-3-phenoxybenzyl (1R,cis)-2,2-dimethyl-3-(2,2-dibromovinyl)cyclopropanecarboxylate or alpha-cyano-3-phenoxybenzyl (+)-S-alpha-isopropyl-p-chlorophenylacetate, the pesticidally most active single stereoisomer is the one which is recovered by the process of the invention in a solid phase in a quantity (substantially) in excess of the amount originally present in a starting diastereoisomer mixture.

The epimerization reaction is conducted in a solvent from which the desired stereoisomer preferentially crystallizes. Suitable solvents are hydroxylic solvents, e.g., lower alkanols containing from 1 to 4 carbon atoms such as isopropanol, butanol, ethanol, and methanol, and preferably containing from 1 to 2 carbon atoms, especially methanol. Lower alkanes containing 1 to 8 carbon atoms, especially containing 5 to 8 carbon atoms, may also be used as solvents such as pentane, hexane, heptane and octane, including isomeric forms thereof. Mixtures of the above kinds of solvents may also be used. For best results, the differential solubilities of the various diastereoisomers or enantiomer pairs in the solvent should be high.

The epimerization catalyst is any base, e.g., inorganic or organic in nature, which does not itself form stable reaction products with the cyanohydrin ester and preferably has a $pK_b$ of less than 5. Examples of suitable inorganic compounds include hydroxides, carbonates, and cyanides of alkali and alkaline earth metals such as sodium cyanide, barium hydroxide, potassium hydroxide, calcium carbonate, sodium carbonate and the like.

Suitable organic bases are alkali or alkaline earth metal salts of weak organic acids or organic nitrogen bases. Suitable salts include sodium acetate, magnesium formate and the like. Nitrogen bases can be any alkyl, aryl or heterocyclic nitrogen base including mono- or polyamines and the like. Preferably, the organic nitrogen base is an amine in which any alkyl groups contain from 1 to 10 carbon atoms, any aryl or aralkyl groups contain from 6 to 20 carbon atoms and 1 to 2 hydrocarbyl rings, and any heterocyclic amines contain at least one ring nitrogen atom in a 5 or 6 membered heterocyclic ring optionally containing a sulfur or oxygen atom or another nitrogen atom such as trimethylamine, triethylamine, piperidine, isoamylamine, benzylamine, diethylamine, tri-n-propylamine, tert-butylamine, ethanolamine, tetramethylenediamine, pyridine or morpholine. The amines are preferably secondary and especially tertiary amines containing any combination of the above-described groups. When the amine is a tertiary amine it desirably contains three alkyl groups of 1 to 4 carbon atoms, for example: trimethylamine, tri-n-propylamine, and especially triethylamine.

The concentration of the epimerization catalyst is not critical. It may vary from 0.01 to 50 mole % based on the amount of the starting material to be converted, preferably, 0.05 to 20 mole % and, especially 0.1 to 15%. Normally about 10% is used.

The reaction is conducted by preparing a solution of the racemate or diastereoisomer mixture in a suitable solvent as defined above and adding the desired amount of epimerization catalyst to the solution. The epimerization (and crystallization) proceeds normally over a period of time, usually several days. The process can be conducted at any temperature at which (crystals of) the desired single stereoisomer or enantiomer pair may form, suitably −50° to 20° C. and preferably −15° to 5° C.

Separation and recovery of the syrup or solid (crystalline) product from the epimerization reaction can be achieved by methods such as extraction, filtration, centrifugation or decantation of the mother liquor. The mother liquor can then be combined with fresh quantities of racemate or diastereoisomer mixture, and this mixture is again subjected to epimerization under conditions previously described.

To reduce the time required to recover the single stereoisomer or enantiomer pair, it is useful to effect alternate cooling, separation of the stereoisomer or enantiomer pair crystals, e.g., by filtering, and then warming the mother liquor to about 50° C. followed by rapid cooling This can be repeated several times. Seeding the reaction mixture with a small amount of crystals of relatively pure desired stereoisomer or enantiomer pair product facilitates crystallization, but is not required.

DESCRIPTION OF THE PREFERRED EMBODIMENT

The preferred embodiment of this invention is based on the finding that the addition of a stabilizing amount of an acid to the solid (substantially pure) single stereoisomer of a cyanohydrin ester, or to a solution thereof in a solvent, functions to prevent reverse base-catalyzed epimerization toward a diastereoisomer mixture. This is useful, e.g., during recrystallization, storage or formulation, of the product stereoisomer. While the precise amount of acid to stabilize the stereoisomer may vary depending upon the particular cyanohydrin ester stereoisomer, from about 0.001 to about 5% by weight of acid based on the stereoisomer is generally sufficient. Preferably, from 0.01 to 0.5% by weight of acid is used.

Any inorganic or organic acid or acidic acting material can be used, which will impart an acidic character to the cyanohydrin ester or solution thereof, including acidic clays such as acidic silicates and aluminates or synthetic acidified clays, mineral acids such as hydrochloric or sulfuric acid, sulfonic acids such as toluenesulfonic acid, or organic acids, including lower alkanoic acids containing from 1 to 7 or preferably 2 to 4 carbon atoms, such as acetic, propionic or butyric acids. The acid can be used in a solid or liquid form.

Stabilized pesticidal formulations not only include a pesticidally effective single stereoisomer of a cyanohydrin pyrethroid ester and stabilizing acidic material but can also contain solvents, surface-active agents and the like. When the stabilizing material is an acidic clay, it can also serve as the carrier. When the stabilizing agent is an acidic surface-active agent, e.g., acidic emulsifier, it can serve as both the stabilizer and emulsifier.

The solvent is usefully any of the solvents normally employed in the epimerization process used to prepare the single stereoisomer or any agriculturally acceptable solvent.

Examples of suitable classes of solvents include chlorinated hydrocarbons, ethers, nitriles, esters, hydroxylic solvents and the like. Suitable hydroxylic solvents include lower alkanols containing from 1 to 4 carbon atoms such as isopropanol, butanol, ethanol, and methanol, and preferably containing from 1 to 2 carbon atoms, especially methanol. Other suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene. Ethers are generally those containing from 4 to 6 carbon atoms such as diethyl ether, methyl tert-butyl ether and diisopropyl ether. Tetrahydrofuran and dioxane are also useful. Nitriles usually also contain from 2 to 6 carbon atoms, for example, acetonitrile and the like. Esters are those of lower alcohols and acids each containing from 2 to 6 carbon atoms, for example, ethyl acetate.

The present compositions comprise cyanohydrin esters of the pyrethroid type. The cyanohydrin esters which can be used in the invention include those cyanohydrin esters having the formula I

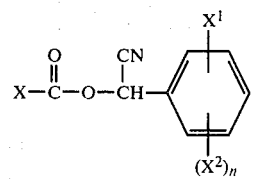

wherein X is a substituted benzyl or a substituted cyclopropyl group containing at least one asymmetric carbon atom, $X^1$ is phenoxy, benzyl or phenylthio, $X^2$ is a halogen atom having an atomic number of from 9 to 35, inclusive, or is methyl and n is 0, 1 or 2.

Preferred because of their pesticidal properties are those pyrethroid esters of formula I wherein n is 0 and $X^1$ is located in the 3-position relative to the benzyl carbon atom in the alcohol moiety. Especially useful are those pyrethroid esters of formula I wherein $X^1$ is phenoxy.

When X represents a substituted benzyl group in formula I, preferred compounds are those containing a substituted benzyl group of the formula II

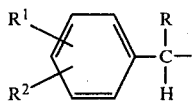

wherein R is an alkyl, cycloalkyl or alkenyl group containing up to 4 carbon atoms and $R^1$ is a hydrogen atom, a halogen atom having an atomic number of from 9 to 53, inclusive, or an alkyl group containing from 1 to 4 carbon atoms or an alkoxy group containing from 1 to 2 carbon atoms, each optionally substituted by one or more halogen atoms having an atomic number of from 9 to 53, inclusive, and $R^2$ is a hydrogen atom or a methyl group.

Preferred because of their pesticidal properties are those pyrethroids wherein X is a substituted benzyl group of formula II in which R is a ranched-chain alkyl or alkenyl group containing 3 or 4 carbon atoms, such as isopropyl or isopropenyl, $R^1$ is a halogen atom or an alkyl or alkoxy group as defined above, for example, $R^1$ is a chlorine or fluorine atom, methyl, ethyl, isopropyl, tert-butyl, methoxy, ethoxy, difluoromethoxy or trifluoromethoxy and $R^2$ is a hydrogen atom. $R^1$ can be located at the meta- or para-position relative to the benzyl carbon atom in the acid moiety. Preferably, $R^1$ is located at the para-position.

When X represents a substituted cyclopropyl group in formula I, preferred compounds are those containing a cyclopropyl group of the formula III

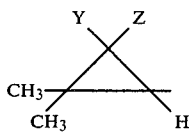

wherein Y and Z each is a halogen atom having an atomic number of from 9 to 35, inclusive, or Y is a halogen atom, an isobutenyl group, a 2,2-dihalovinyl group in which each halo is a halogen atom having an atomic number of from 9 to 35, inclusive, and Z is a hydrogen atom.

Preferred because of their pesticidal properties are those pyrethroids wherein X is a cyclopropyl group of formula III in which Y and Z each is chlorine or Y is chlorine, isobutenyl, 2,2-dichlorovinyl or 2,2-dibromovinyl and Z is a hydrogen atom.

In the case of the cyanohydrin esters described above, a single stereoisomer is prepared by contacting a diastereoisomer mixture with a base as an epimerization catalyst, in the presence of a solvent from which said stereoisomer preferentially crystallizes, at a temperature below the melting point of the desired single stereoisomer, to obtain the single desired stereoisomer (in high purity) in a solid phase, in a quantity (substantially) in excess of the amount originally present in the starting diastereoisomer mixture.

For example, in the case of either of the above-mentioned two esters, alpha-cyano-3-phenoxybenzyl (1R,cis)-2,2-dimethyl-3-(2,2-dibromovinyl)cyclopropanecarboxylate or alpha-cyano-3-phenoxybenzyl (+)-S-alpha-isopropyl-p-chlorophenylacetate, the pesticidally most active single stereoisomer is the one which is recovered by the process of the invention in a solid phase in a quantity (substantially) in excess of the amount originally present in a starting diastereoisomer mixture.

A diastereoisomer mixture of cyanohydrin esters for the purpose of the method of the present application is defined as one in which the diastereoisomers differ in configuration only at the asymmetric carbon atom in the alcohol moiety containing the cyano substituent.

The epimerization reaction is conducted in a solvent from which the desired stereoisomer preferentially crystallizes. Suitable solvents are hydroxylic solvents, e.g., lower alkanols containing from 1 to 4 carbon atoms such as isopropanol, butanol, ethanol, and methanol, and preferably containing from 1 to 2 carbon atoms, especially methanol. Lower alkanes containing 1 to 8 carbon atoms, especially containing 5 to 8 carbon atoms, may also be used as solvents such as pentane, hexane, heptane, and octane, including the isomeric forms thereof. Mixtures of the above kinds of solvents may also be used. For best results, the differential solubilities of the various diastereoisomers in the solvent should be high.

The epimerization catalyst is any base, e.g., inorganic or organic in nature, which does not itself form stable reaction products with the cyanohydrin ester and preferably has a $pK_b$ of less than 5. Examples of suitable inorganic compounds include hydroxides, carbonates, and cyanides of alkali and alkaline earth metals such as sodium cyanide, barium hydroxide, potassium hydroxide, calcium carbonate, sodium carbonate and the like.

Suitable organic bases are alkali or alkaline earth metal salts of weak organic acids or organic nitrogen bases. Suitable salts include sodium acetate, magnesium formate and the like. Nitrogen bases can be any alkyl, aryl or heterocyclic nitrogen base including mono- or polyamines and the like. Preferably, the organic nitrogen base is an amine in which any alkyl groups contain from 1 to 10 carbon atoms, any aryl or aralkyl groups contain from 6 to 20 carbon atoms and 1 to 2 hydrocarbyl rings, and any heterocyclic amines contain at least one ring nitrogen atom in a 5 or 6 membered heterocyclic ring optionally containing a sulfur or oxygen atom or another nitrogen atom such as trimethylamine, triethylamine, piperidine, isoamylamine, benzylamine, diethylamine, tri-n-propylamine, tert-butylamine, ethanolamine, tetramethylenediamine, pyridine or morpholine. The amines are preferably secondary and especially tertiary amines containing any combination of the above-described groups. When the amine is a tertiary amine it desirably contains three alkyl groups of 1 to 4 carbon atoms, for example: trimethylamine, tri-n-propylamine, and especially triethylamine.

The concentration of the epimerization catalyst is not critical. It may vary from 0.01 to 50 mole % based on the amount of the starting reactant diastereoisomer to be converted, preferably, 0.05 to 20 mole % and, especially 0.1 to 15%. Normally about 10% is used.

The reaction is conducted by preparing a solution of the diastereoisomer mixture in a suitable solvent as defined above and adding the desired amount of epimerization catalyst to the solution. The epimerication and crystallization proceeds normally over a period of time, usually several days. The process can be conducted at any temperature at which crystals of the desired single stereoisomer may form, suitably −50° to 20° C. and preferably −15° to 5° C.

Separation and recovery of the solid (crystalline) product from the epimerization reaction can be achieved by methods such as filtration, centrifugation or decantation of the mother liquor. The mother liquor can then be combined with fresh quantities of diastereoisomer mixture, and this mixture is again subjected to epimerization under conditions previously described.

To reduce the time required to recover the single stereoisomer, it is useful to effect alternate cooling, separation of the stereoisomer crystals, e.g., by filtering, and then warming the mother liquor to about 50° C. followed by rapid cooling. This can be repeated several times. Seeding the reaction mixture with a small amount of crystals of relatively pure desired stereoisomer product facilitates crystallization, but is not required.

Illustrative Embodiments

The following embodiments are provided for the purpose of illustrating the invention and should not be regarded as limiting it in any way. The identity of the products was confirmed by infrared and nuclear magnetic resonance spectral analyses as necessary.

Embodiment I

A solution of 10.0 g of essentially equimolar amounts of the diastereoisomer pair, (±)-R,S-α-cyano-3-phenoxybenzyl (+)-S-α-isopropyl-p-chlorophenylacetate, and 0.1 ml of triethylamine in 40 ml of methanol was cooled to −10° C. and seeded with a small amount of crystals of (−)-S-α-cyano-3-phenoxybenzyl (+)-S-α-isopropyl-p-chlorophenylacetate. The mixture was kept cool for 5 days by which time more crystals had formed from the mixture in solution. The mixture was filtered and 8.2 g of solid (−)-S-α-cyano-3-phenoxybenzyl (+)-S-α-isopropyl-p-chlorophenylacetate, m.p. 60° C., was recovered.

Embodiment II

An essentially equimolar mixture of 120 mg (±)-R,S-α-cyano-3-phenoxybenzyl (1R,cis)-2,2-dimethyl-3-(2,2-dibromovinyl)cyclopropanecarboxylate was dissolved in 0.5 ml of methanol and 2 μl of trimethylamine was added. The mixture was kept at 5° C. overnight and, after being cooled at −10° C. for one hour, 76.6 mg of solid (−)-S-α-cyano-3-phenoxybenzyl (1R,cis)-2,2-dimethyl-3-(2,2-dibromovinyl)cyclopropanecarboxylate was obtained. Evaporation of the methanol filtrate gave 41.1 mg of the (±)-R,S-alcohol (1R,cis)-acid ester mixture. The two products were recombined in 0.5 ml of methanol, treated with 2 μl of triethylamine and stored at −10° C. for 6 days after which 87.3 mg of solid (−)-S-α-cyano-3-phenoxybenzyl (1R,cis)-2,2-dimethyl-3-(2,2-dibromovinyl)cyclopropanecarboxylate was obtained; m.p.: 98°–99° C.

In like manner, a single solid stereoisomer of α-cyano-3-phenoxybenzyl 2,2-dimethyl-3-(2,2-dichlorovinyl)cyclopropanecarboxylate or α-cyano-3-phenoxybenzyl 2,2-dimethyl-3-isobutenylcyclopropanecarboxylate is obtained from a normally liquid solution containing a mixture of diastereoisomers of such carboxylate.

Embodiment III

To a 10% solution prepared using crystalline (−)-S-α-cyano-3-phenoxybenzyl (+)-S-α-isopropyl-p-chlorophenylacetate dissolved in reagent grade methanol was added about 1% of acetic acid relative to the methanol. The solution was warmed without any sign of epimerization.

In contrast, a saturated solution of the above crystalline ester in reagent grade methanol but without addition of acetic acid, warmed to dissolve the ester and cooled at once showed about 50% epimerization. Likewise, a solution prepared by dissolving the crystalline ester in reagent grade methanol epimerized with a half-life of about two hours when no acetic acid or other acidic material was added to the solution maintained at room temperature.

We claim:

1. A pesticidal composition comprising an insecticidally effective amount of a non-racemic form of a cyanohydrin ester of the formula

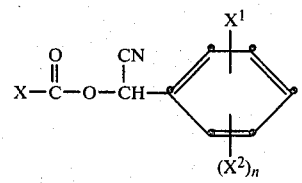

wherein X is
(a) a substituted benzyl group of the formula

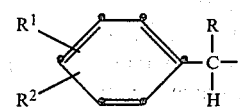

wherein R is an alkyl, cycloalkyl or alkenyl group containing up to 4 carbon atoms; $R^1$ is a hydrogen atom, a halogen atom having an atomic number of from 9 to 35, inclusive, an alkyl group containing from 1 to 4 carbon atoms or an alkoxy group containing from 1 to 2 carbon atoms, each optionally substituted by one or more halogen atoms having an atomic number of from 9 to 35, inclusive, and $R^2$ is a hydrogen atom or a methyl group, or (b) a substituted cyclopropyl group of the formula

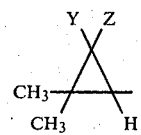

wherein Y and Z each is a halogen atom having an atomic number of from 9 to 35, inclusive, Y is a halogen atom, an isobutenyl group or a 2,2-dihalovinyl group in which each halo is a halogen atom having an atomic number of from 9 to 35, inclusive, and Z is a hydrogen atom; $X^1$ is phenoxy, benzyl or phenylthio, $X^2$ is a halogen atom having an atomic number of from 9 to 35, inclusive, or is methyl and n is 0, 1 or 2, which contains at least one asymmetric carbon atom in each of the acid and alcohol moieties, or a solution of the non-racemic ester in a solvent from an epimerization process or in an agriculturally acceptable solvent and a stabilizing amount of lower alkanoic acid to prevent epimerization of said ester.

2. A composition according to claim 1 wherein X is a substituted benzyl group in which R is a branched-chain alkyl or alkenyl group containing 3 to 4 carbon atoms; $X^1$ is located at the 3-position relative to the benzyl carbon atom in the alcohol moiety and n is 0.

3. A composition according to claim 2 wherein R is isopropyl; or isopropenyl; $R^1$ is chlorine, fluorine, methyl, ethyl, isopropyl, tert-butyl, methoxy, ethoxy, difluoromethoxy or trifluoromethoxy; $R^2$ is hydrogen and $X^1$ is phenoxy.

4. A composition according to claim 3 wherein R is isopropyl; $R^1$ is para-chloro; $R^2$ is hydrogen; $X^1$ is 3-phenoxy; and n is 0.

5. A composition according to claim 1 wherein X is a cyclopropyl group in which Y and Z each is chlorine or Y is chlorine, isobutenyl, dichlorovinyl or dibromovinyl and Z is a hydrogen atom.

6. A composition according to claim 5 wherein Y is dibromovinyl and Z is a hydrogen atom.

7. A composition according to claim 1 wherein the acid is present in the composition in an amount of from 0.001 to 5% by weight of the acid based on the amount of non-racemic ester.

8. A composition according to claim 1 wherein the lower alkanoic acid is acetic acid.

9. A composition according to claim 8 wherein the acetic acid is present in the composition in an amount of from 0.01 to 0.5% by weight of the acid based on the non-racemic ester.

10. An insecticidal composition comprising an insecticidally effective amount of a solid single stereoisomer of a cyanohydrin ester of the formula

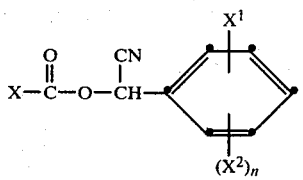

wherein X is
(a) a substituted benzyl group of the formula

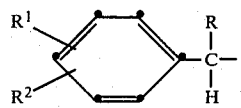

wherein R is an alkyl, cycloalkyl or alkenyl group containing up to 4 carbon atoms; $R^1$ is a hydrogen atom, a halogen atom having an atomic number of from 9 to 35 inclusive, an alkyl group containing from 1 to 4 carbon atoms or an alkoxy group containing from 1 to 2 carbon atoms, each optionally substituted by one or more halogen atoms having an atomic number of from 9 to 35, inclusive, and $R^2$ is a hydrogen atom or a methyl group, or
(b) a substituted cyclopropyl group of the formula

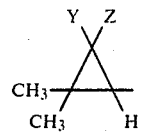

wherein Y and Z each is a halogen atom having an atomic number of from 9 to 35, inclusive, Y is a halogen atom, an isobutenyl group or a 2,2-dihalovinyl group in which each halo is a halogen atom having an atomic number of from 9 to 35, inclusive, and Z is a hydrogen atom; $X^1$ is phenoxy, benzyl, phenylthio; $X^2$ is a halogen atom having an atomic number of from 9 to 35, inclusive, or is methyl and n is 0, 1 or 2, which contains at least one asymmetric carbon atom in each of the acid and alcohol moieties, or a solution of the stereoisomer in a solvent from an epimerization process or in an agriculturally acceptable solvent and a stabilizing amount of a lower alkanoic acid to prevent epimerization of said stereoisomer.

11. A composition according to claim 10 wherein X is a substituted benzyl group in which R is a branched-chain alkyl or alkenyl group containing 3 to 4 carbon atoms; $X^1$ is located at the 3-position relative to the benzyl carbon atom in the alcohol moiety and n is 0.

12. A composition according to calim 11 wherein R is isopropyl; or isopropenyl; $R^1$ is chlorine, fluorine, methyl, ethyl, isopropyl, tert-butyl, methoxy, ethoxy, difluoromethoxy or trifluoromethoxy; $R^2$ is hydrogen and $X^1$ is phenoxy.

13. A composition according to claim 12 wherein R is isopropyl; $R^1$ is para-chloro; $R^2$ is hydrogen; $X^1$ is 3-phenoxy; n is 0 and the acid moiety is in the (+)-S-stereoisomeric configuration and the alcohol moiety in the (−)-S-stereoisomer configuration.

14. A composition according to claim 10 wherein X is a cyclopropyl group in which Y and Z each is chlorine or Y is chlorine, isobutenyl, dichlorovinyl or dibromovinyl and Z is a hydrogen atom.

15. A composition according to claim 14 wherein Y is dibromovinyl and Z is a hydrogen atom.

16. A composition according to claim 10 wherein the acid is present in the composition in an amount of from 0.001 to 5% by weight of the acid based on the stereoisomer.

17. A composition according to claim 10 wherein the lower alkanoic acid is acetic acid.

18. A composition according to claim 17 wherein the acetic acid is present in the composition in an amount of from 0.01 to 0.5% by weight of the acid based on the stereoisomer.

19. An insecticidal composition comprising an insecticidally effective amount of a solid substantially pure (−)-S-α-cyano-3-phenoxy-benzyl (+)-S-α-isopiopyl-p-chlorophenylacetate or a solution thereof in methanol and a stabilizing amount of a lower alkanoic acid to prevent epimerization of said acetate.

20. A composition according to claim 19 wherein the lower alkanoic acid is present in the composition in an amount of from 0.001 to 5% by weight of the acid based on the stereoisomer.

21. A composition according to claim 20 wherein the lower alkanoic acid is acetic acid, which is present in the composition in an amount of from 0.01 to 0.5% by weight of the acid based on the stereoisomer.

22. A method of stabilizing an insecticidally effective non-racemic cyanohydrin ester of the formula

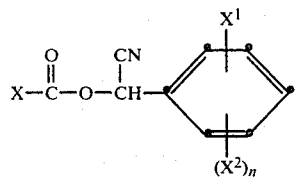

wherein X is
(a) a substituted benzyl group of the formula

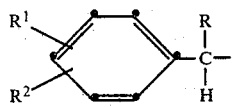

wherein R is an alkyl, cycloalkyl or alkenyl group containing up to 4 carbon atoms; $R^1$ is a hydrogen atom, a halogen atom having an atomic number of from 9 to 35 inclusive, an alkyl group containing from 1 to 4 carbon atoms or an alkoxy group containing from 1 to 2 carbon atoms, each optionally substituted by one or more halogen atoms having an atomic number of from 9 to 35, inclusive, and $R^2$ is a hydrogen atom or a methyl group, or (b) a substituted cyclopropyl group of the formula

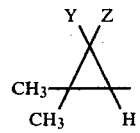

wherein Y and Z each is a halogen atom having an atomic number of from 9 to 35, inclusive, Y is a halogen atom, an isobutenyl group or a 2,2-dihalovinyl group in which each halo is a halogen atom having an atomic number of from 9 to 35, inclusive, and Z is a hydrogen atom; $X^1$ is phenoxy, benzyl phenylthio; $X^2$ is a halogen atom having an atomic number of from 9 to 35, inclusive, or is methyl and n is 0, 1 or 2, which contains at least one asymmetric carbon atom in each of the acid and alcohol moieties, or a solution of the non-racemic ester in a solvent from an epimerization process or in an agriculturally acceptable solvent, which method comprises adding a stabilizing amount of a lower alkanoic acid to the non-racemic ester or solution thereof to prevent epimerization of said ester.

23. A method according to claim 22 wherein the lower alkanoic acid is acetic acid.

24. A method according to claim 22 wherein the acid is used in an amount of from 0.001 to 5% by weight of acid based upon the non-racemic ester.

25. A method according to claim 24 wherein the acid is used in an amount of from 0.01 to 0.5% by weight of acid based upon the non-racemic ester.

26. A method of stabilizing a solid single stereoisomer of a cyanohydrin ester of the formula

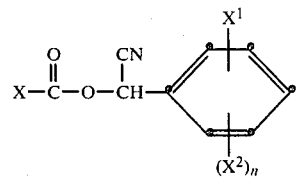

wherein X is
(a) a substituted benzyl group of the formula

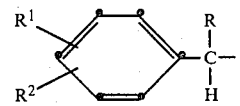

wherein R is an alkyl, cycloalkyl or alkenyl group containing up to 4 carbon atoms; $R^1$ is a hydrogen atom, a halogen atom having an atomic number of from 9 to 35 inclusive, an alkyl group containing from 1 to 4 carbon atoms or an alkoxy group containing from 1 to 2 carbon atoms, each optionally substituted by one or more halogen atoms having an atomic number of from 9 to 35, inclusive, and $R^2$ is a hydrogen atom or a methyl group, or (b) a substituted cyclopropyl group of the formula

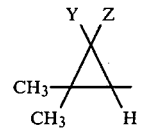

wherein Y and Z each is a halogen atom having an atomic number of from 9 to 35, inclusive, Y is a halogen atom, an isobutenyl group or a 2,2-dihalovinyl group in which each halo is a halogen atom having an atomic number of from 9 to 35, inclusive, and Z is a hydrogen atom; $X^1$ is phenoxy, benzyl phenylthio; $X^2$ is a halogen atom having an atomic number of from 9 to 35, inclusive, or is methyl and n is 0, 1 or 2, which contains at least one asymmetric carbon atom in each of the acid and alcohol moieties, or a solution of the stereoisomer in a solvent from an epimerization process or in an agriculturally acceptable solvent; which comprises adding a stabilizing amount of a lower alkanoic acid to said stereoisomer or solution thereof to prevent epimerization of said stereoisomer.

27. A method according to claim 26 wherein the lower alkanoic acid is acetic acid.

28. A method according to claim 26 wherein the acid is used in an amount of from 0.001 to 5% by weight of acid based on the stereoisomer.

29. A method according to claim 28 wherein the acid is used in an amount of from 0.01 to 0.5% by weight of acid based on the stereoisomer.

* * * * *